United States Patent
Garcia et al.

(10) Patent No.: US 9,284,110 B2
(45) Date of Patent: Mar. 15, 2016

(54) SURGICAL SCREW CARTRIDGE FOR RAPIDLY AND ACCURATELY LOADING SURGICAL SCREWS ONTO A DRIVER

(71) Applicants: Saddy R. Garcia, Saint Augustine, FL (US); Bradley Winterroth, Wesley Chapel, FL (US); Larry Miller, Ponte Vedra Beach, FL (US)

(72) Inventors: Saddy R. Garcia, Saint Augustine, FL (US); Bradley Winterroth, Wesley Chapel, FL (US); Larry Miller, Ponte Vedra Beach, FL (US)

(73) Assignee: Zimmer Biomet CMF and Thoracic, LLC, Jacksonville, FL (US)

( * ) Notice: Subject to any disclaimer, the term of this patent is extended or adjusted under 35 U.S.C. 154(b) by 267 days.

(21) Appl. No.: 13/767,929

(22) Filed: Feb. 15, 2013

(65) Prior Publication Data
US 2014/0069952 A1      Mar. 13, 2014

Related U.S. Application Data

(63) Continuation of application No. 12/459,024, filed on Jun. 25, 2009, now Pat. No. 8,377,074.

(51) Int. Cl.
| | |
|---|---|
| *A61B 17/04* | (2006.01) |
| *A61B 17/86* | (2006.01) |
| *A61F 2/08* | (2006.01) |
| *B65D 83/02* | (2006.01) |
| *B25B 23/00* | (2006.01) |
| *B25B 23/06* | (2006.01) |

(52) U.S. Cl.
CPC .............. *B65D 83/02* (2013.01); *A61B 17/865* (2013.01); *B25B 23/00* (2013.01); *B25B 23/06* (2013.01); *B25B 23/065* (2013.01); *Y10T 29/49778* (2015.01)

(58) Field of Classification Search
CPC ...... B25B 23/00; B25B 23/06; B25B 23/065; B65D 83/02; A61B 17/865
USPC ..................... 81/57.37, 177.4, 451–453, 490; 606/104, 301–321; 221/279–280
See application file for complete search history.

(56) References Cited

U.S. PATENT DOCUMENTS

| | | | |
|---|---|---|---|
| 1,537,929 A * | 5/1925 | Lee .................................. | 81/125 |
| 1,543,175 A * | 6/1925 | McCarthy ........................ | 81/125 |
| 7,650,991 B2 | 1/2010 | Hester et al. | |
| 2007/0119871 A1 * | 5/2007 | Garcia .......................... | 222/325 |

\* cited by examiner

*Primary Examiner* — David Bates
*Assistant Examiner* — Olivia C Chang
(74) *Attorney, Agent, or Firm* — Schwegman Lundberg & Woessner, P.A.

(57) ABSTRACT

A surgical screw cartridge system apparatus and method is provided wherein the cartridge has a body for storing a plurality of surgical screws. A spring-biased plunger is positioned within the body for presenting the surgical screws head first to a driver. A tab within the body prevents removal of the surgical screws from the body in absence of a screwdriver.

10 Claims, 3 Drawing Sheets

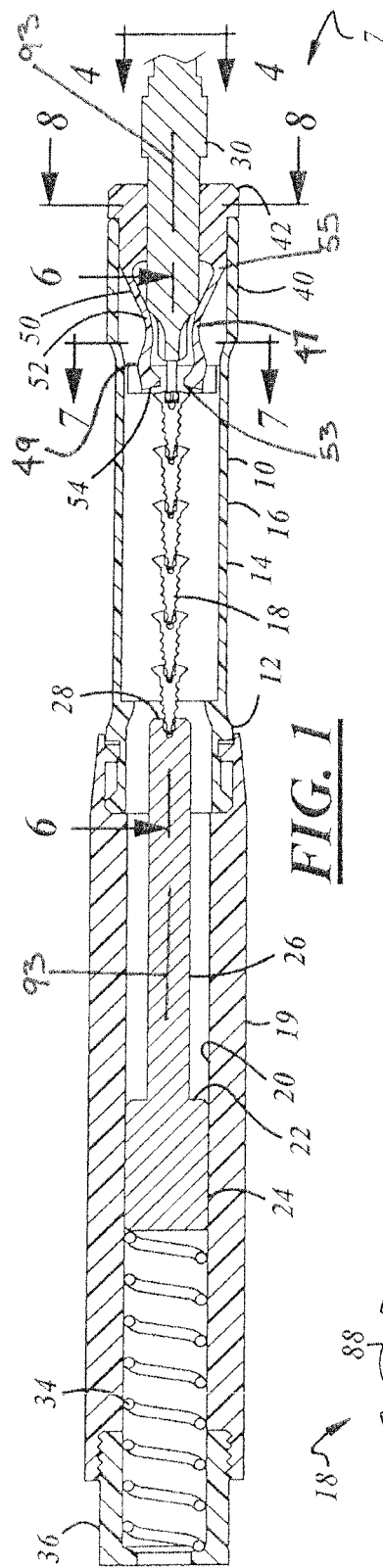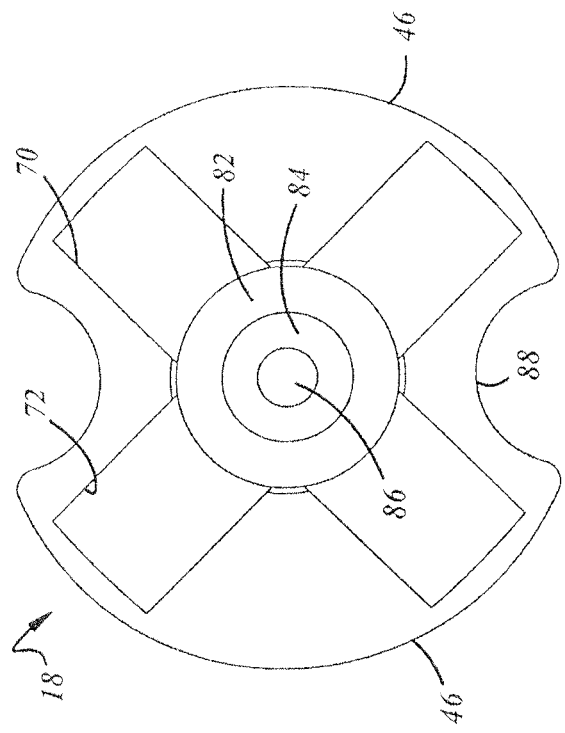

SURGICAL SCREW CARTRIDGE FOR RAPIDLY AND ACCURATELY LOADING SURGICAL SCREWS ONTO A DRIVER

This application is a Continuation Application of U.S. patent application Ser. No. 12/459,024, filed Jun. 25, 2009. The disclosure of the above application is incorporated herein by reference.

FIELD OF THE INVENTION

The present invention relates to surgical screw systems utilized for the fixation of bones.

BACKGROUND OF THE INVENTION

During surgical operations involving fixation of bones, it is highly desirable that a surgical screw system be provided that allows a loading of the surgical screw to a surgical screwdriver in a fast, efficient manner.

SUMMARY OF THE INVENTION

To make manifest the above noted and other manifold desires, a revelation of the present invention is brought forth. In a preferred embodiment, the present invention brings forth a surgical screw system that provides a surgical screw cartridge having a body for storing a plurality of surgical screws. A spring-biased plunger is provided within the cartridge body for presenting the surgical screws head first to a screwdriver. A tab is also provided which prevents removal of the surgical screw from the cartridge in the absence of the screwdriver.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein:

FIG. 1 is a sectional view of a preferred embodiment screw cartridge according to the present invention;

FIG. 2 is an enlarged side elevational view of a surgical screw utilized in the screw cartridge system according to the present invention;

FIG. 3 is an enlarged top plan view of the surgical screw shown in FIG. 2;

DETAILED DESCRIPTION OF THE PREFERRED EMBODIMENTS

Figure 4:
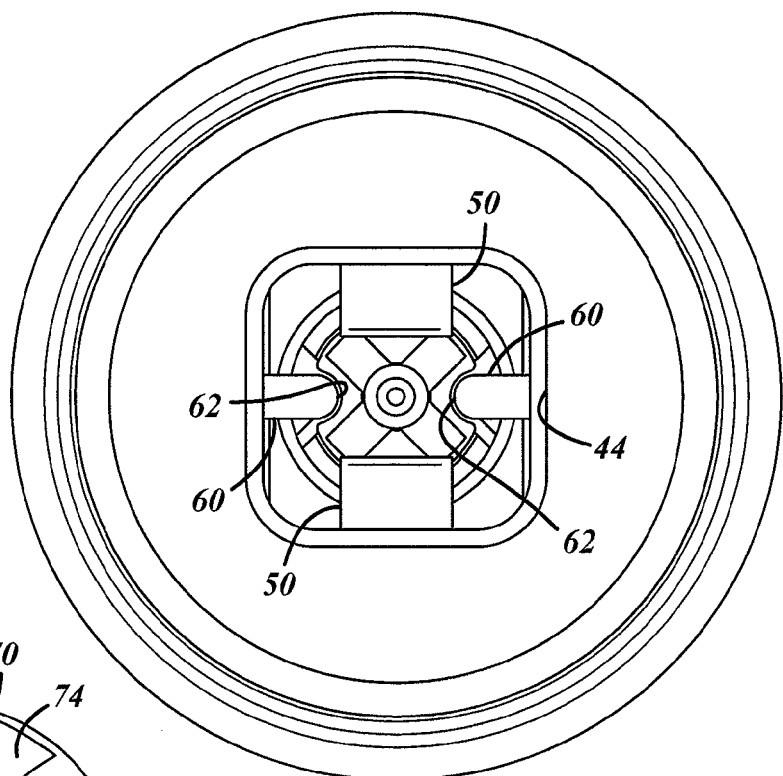
FIG. 4 is a view taken along line 4-4 of the screw cartridge shown in FIG. 1 with a surgical screwdriver removed for clarity of illustration.

The following description of the preferred embodiment(s) is merely exemplary in nature and is in no way intended to limit the invention, its application, or uses.

Referring to FIG. 1, the surgical screw system 7 according to the present invention has a cartridge 10. The cartridge 10 has a body 12 which is typically fabricated from metal or plastic. The body 12 has an upper portion 14 with an upper central cavity 16. The cavity 16 is provided for storage of a plurality of surgical screws 18.

The cartridge 10 also has a lower portion 19. The cartridge lower portion 19 has a central cavity 20 generally aligned concentrically with the central cavity 16. Slidably mounted within the cavity 20 is a plunger 22. Typically, the plunger 22 is fabricated from metal or a plastic material. The plunger has a lower cylindrical alignment portion 24 slidably mounted within the cavity 20 along a linear axis of travel 93. Connected on top of the plunger alignment portion 24 is an extended stem 26. The plunger stem 26 has on its upper end a multi-diameter complex counterbore 28 to allow the plunger to hold the lowest surgical screw 18.

Biasing the plunger 22 to allow the plunger 22 to present a surgical screw 18 head first to a surgical driver 30 is a coil spring 34. Retaining the coil spring 34 in position is a threadably connected lower body cap 36. If desired, cap 36 can be screwed in or out to adjust the compression on the spring 34.

The body 12 has an upper portion 40 provided in part by an alignment cap 42. The alignment cap 42 has a generally rectangular opening 44. The opening 44 positionally aligns the driver 30 with a head 46 provided on the surgical screws 18.

The alignment cap 42 also has integrally connected thereto opposed tabs 50. Tabs 50 have an upper neck portion 52 and a lower blocker portion 54. The tabs 50 are cantileverly supported from a first radial position 55. The lower blocker portion 54 contacts the screws 18 at a second radial position 53. From the first radial position 55 the tabs 56 have a first curvaliner shaped section 47 with a radially outward radius of curvature that transitions into a second curvaliner shaped section 49 with a radially inward radius of curvature. The second radial position 53 is less radially distant from the axis of travel 93 than the first radial position 55. The second radial position 53 is also more adjacent to the plunger 22 than the first radial position 56. The lower blocker portion 54 prevents removal of the screws 18 from the body 12 in the absence of the driver 30. Upon the presence of the driver 30, the driver 30 contacts the upper neck portion 52 causing the blocker portion 54 to be urged outwardly.

The body 12 along its upper portion 40 also has two opposing rails 60. The rails 60 have a semi-circular radially inward projecting edge 62. The rails angularly positionally align the screws 18 with the body 12.

The screws 18 have, as mentioned previously, a head 46. The screw head 46 is connected to a generally tapered threaded shank 66 ending in an optional self-drilling or self-tapping tip 68. The screw 18 is typically fabricated from stainless steel, or titanium, or from a bio-absorbable or non-bio-absorbable plastic material. The screw head 46 has a Phillips or "crosshead" type drive, consisting of two generally perpendicular, crossing slots 70 and 72, which are configured for reception of the driver 30 and provide a torsional interface therewith. It is apparent to those skilled in the art that other screw drive configurations can be utilized. The slots 70 and 72 have the same width and have generally conical cross-sectionally shaped floors 74 and 76, respectfully. Separating the slots 72 and 70 are four cylindrical segments 78. The top of the segments 78 have a slight chamfer 80 so as not to damage the threaded shank 66 of an adjoining screw. The cylindrical segments 78 (and the chamfer 80) form a primary surface of a stepped counterbore which accepts the threaded shank 66 of an adjoining screw while at the same time preventing contact of the tips 68. The bottom of cylindrical segments 78 blend with, and the floors 74 and 76 intersect with, a cylindrical wall 81 that perpendicularly intersects with a generally annular flat 82 at an outer perimeter thereof.

Figure 5:
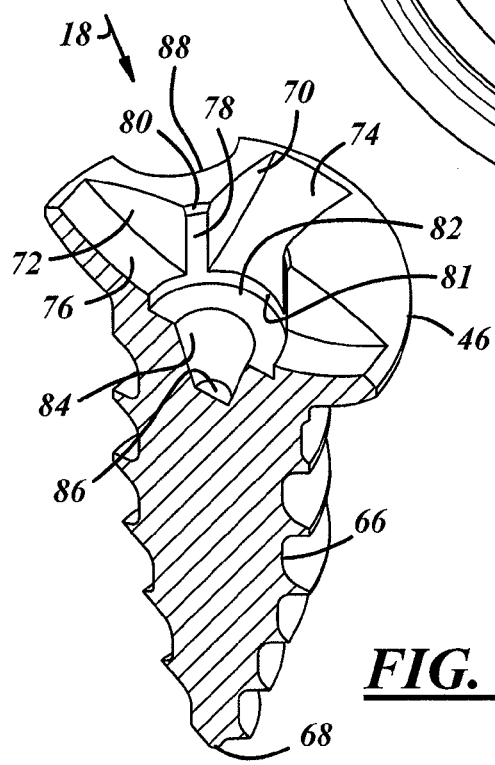
FIG. 5 is an enlarged section perspective view of a surgical screw utilized with the present invention.
Figure 6:
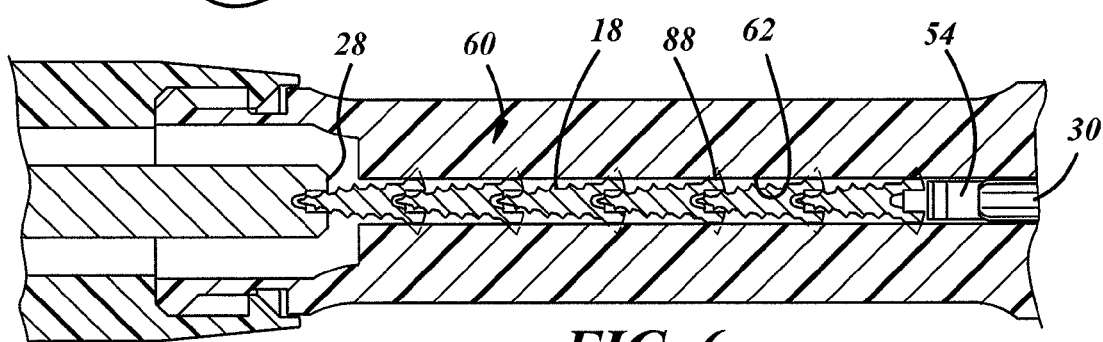
FIG. 6 is a view taken along line 6-6 of FIG. 1 of the screw cartridge according to the present invention.
Figure 7:
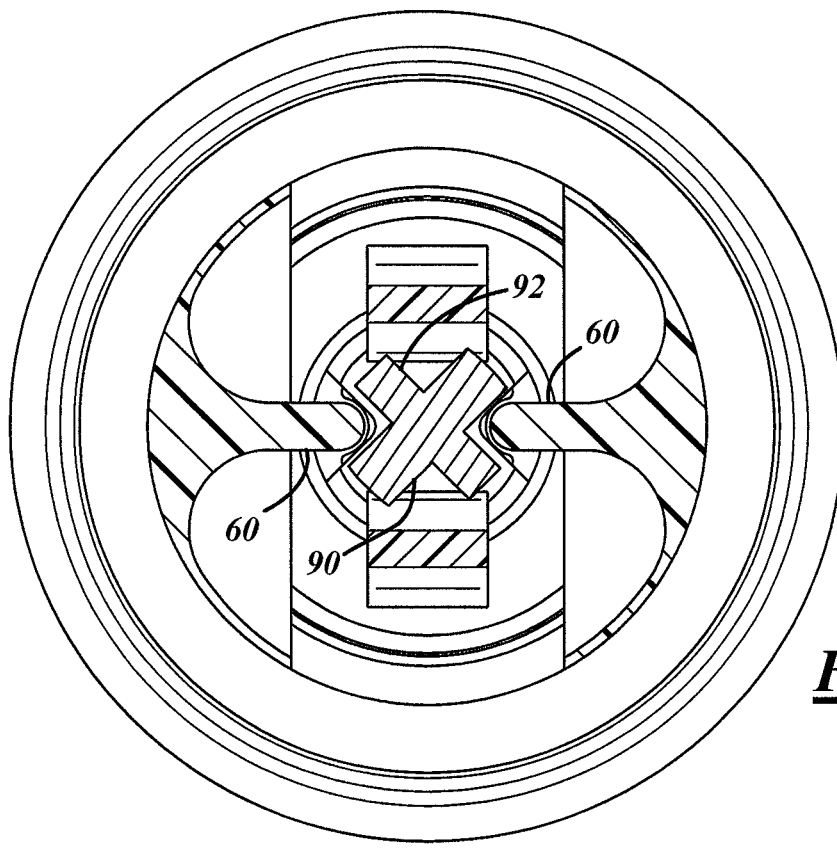
FIG. 7 is a view taken along line 7-7 of FIG. 1 of the screw cartridge according to the present invention.
Figure 8:
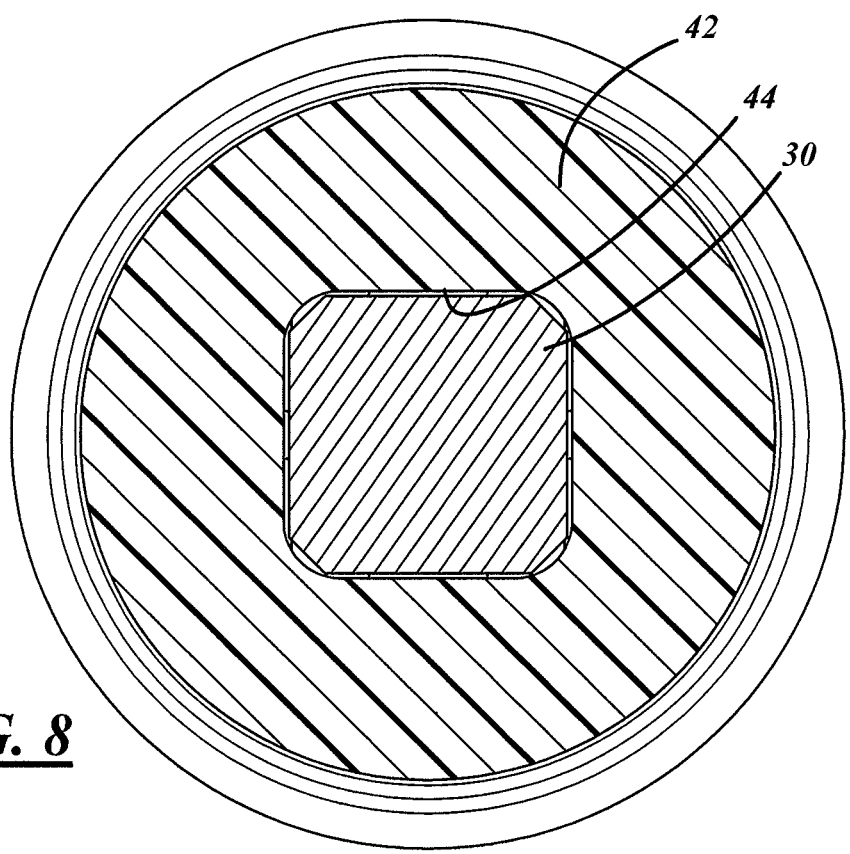
FIG. 8 is a view taken along line 8-8 of FIG. 1 of the screw cartridge shown in FIG. 1 of the present invention.

Intersecting the annular flat 82 at an inner perimeter thereof is a generally conical depression 84. The conical depression 84 has a convergent angle that is greater than a convergent angle of the screw shank 66 adjacent the screw tip 68 to prevent possible wedging of the screw shank 66 with its lower adjacent screw. The conical depression 84 has a floor 86 which is dimensioned so that an adjoining screw 18 will contact the conical depression 84 without the tip 68 contacting the floor 86. The above noted configuration of the conical depression 84 allows it to serve as a secondary contact surface between the adjacent screw in case there is a failure of the cylindrical segment 78 to fully hold up the adjacent screw 18. A counterbore similar to that shown on FIG. 5 with respect to the screw 18 is also provided by the counterbore 28 and the tip of plunger 22, as generally shown in FIG. 6. The screw 18 also has an axial cylindrical segmented groove 88 that is operatively associated with the projecting edges 62 of the rails 60 to allow the rails to angularly position and align the screws 18 within the body 12.

In operation, a surgeon, or another medical professional assisting a surgeon, will take the screwdriver 30 and insert a blade of the screwdriver into the opening 44 provided by the cartridge 10. As will be readily apparent to those skilled in the art, in some instances, it will be more convenient for the surgeon or the medical assistant to take the cartridge 10 by hand and stick it up over the driver 30. The driver 30 will be aligned with the screws 18 inside the cartridge 10 by the opening 44. The screws 18 within the cartridge 10 will be held in a tandem stack. Typically, the cartridge 10 will contain five to six surgical screws. The plunger 22 is biased by the spring 34 to allow the plunger 22 to urge the screws 18 head-first toward the driver 30. The screws 18 will be angularly aligned within the driver 30 by the opposing rails 60. In the absence of the driver 30, the blocker portion 52 of the tabs 50 will prevent removal of the screws 18 from the driver 30. Upon insertion of the driver 30 within the cartridge 10, the driver 30 contacts the upper neck portion 52 of the tabs 50 causing the blocker portions 54 to be moved outwardly. The coil spring 34 is then free to urge or accelerate the plunger 22 towards the driver 30 and in some applications, acceleration of the screws 18 toward the driver 30 generates a confirmatory auditory click and/or tactile vibration signal, thereby allowing the surgeon to recognize that the surgical screw is now contacted with the driver. The driver 30 can in some applications continue to be advanced into the cartridge 10 to further insure complete engagement of screw 18 with the driver 30. The driver blades 90 and 92 are sized relative the slots 70 and 72 of the screw to allow the driver blades 90 and 92 to connect with the screw with a slight interference fit for connecting the screw to the driver 30. After the screw 18 is connected with the driver 30, the surgeon can then remove the screw loaded screwdriver and utilize the screwdriver in a surgical operation. Upon completion of torquing the screw 18 into a patient, the surgeon can then readily reload the next screw with the driver 30 by inserting the driver into the cartridge 10.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A surgical screw cartridge system comprising:
    a body having a cavity for storing a plurality of surgical screws in a tandem manner;
    a biased plunger positioned within said body for presenting a surgical screw head-first to a screwdriver along a linear axis of travel;
    opposing tabs preventing removal of a surgical screw from said body in absence of an insertion of the screwdriver within said body, each said tab being cantileverly supported from first radial position, said tab having a lower blocker portion at a second radial position and wherein said second radial position is less of a radial distance from said plunger linear axis of travel than said first radial position and said second radial position is more adjacent to said plunger than said first radial position and said tabs from said first radial positions to said second radial positions having a first section with a curvilinear shape with an outer radius of curvature transitioning into a second section with an inner radius of curvature.

2. A surgical screw cartridge system as described in claim 1 further including an alignment cap for positioning a screwdriver with respect to said surgical screw within said body.

3. A surgical screw cartridge system as described in claim 1 wherein said plunger is biased by a coil spring.

4. A surgical screw cartridge system as described in claim 1 further including a rail to angularly position said surgical screw within said body.

5. A surgical screw cartridge system as described in claim 1 wherein said plunger has a counterbore for receipt of a tapered threaded portion of said screw without contacting a tip of said surgical screw.

6. A surgical screw cartridge system as described in claim 1 wherein said tabs have upper neck portions and wherein said lower blocker portions prevents removal of surgical screws from said body unless the driver contacts said upper neck portions to cause said blocker portions to be urged outwardly.

7. A surgical screw cartridge system comprising:
    a body having a cavity for storing a plurality of surgical screws in a tandem manner;
    a spring biased plunger having a linear axis of travel, positioned within said body for presenting said surgical screw head-first to a screwdriver, said plunger having a counterbore for receipt of a tapered threaded portion of said surgical screw without contacting a tip of said surgical screw;
    opposing tabs preventing removal of said surgical screw from said body in absence of insertion of a screwdriver into said body, said tabs being cantileverly supported from a first radial position, and said tabs having a lower blocker portion at a second radial position, wherein said second radial position is at a radial distance less than said first radial position from said plunger linear axis of travel, and said second radial position being more adjacent to said plunger than said first radial position, and said tabs from said first radial positions to said second radial positions having a first section with a curvilinear shape with an outer radius of curvature transitioning into a second section with an inner radius of curvature and said tabs having an upper neck portion wherein said lower blocker portion prevents removal of said surgical screw from said body unless the driver contacts said upper neck portions causing said tabs' lower blocker portions to be urged outwardly;
    an alignment cap for positioning the screwdriver with respect to a screw within said body; and
    a rail to angularly position said surgical screw within said body.

8. A surgical screw cartridge system comprising:
    a body having a cavity for storing a plurality of surgical screws in a tandem manner;
    a biased plunger having a linear axis of travel, said plunger being positioned within said body for presenting a surgical screw head-first to a screwdriver;
    opposing tabs preventing removal of a surgical screw from said body in absence of an insertion of the screwdriver within said body, each said tab being cantileverly supported from a first radial position, each said tab having a lower blocker portion at a second radial position and wherein said second radial position is less of a radial distance from said plunger linear axis travel than said first radial position, and said second radial position is more adjacent to said plunger, and said tabs from said first radial positions to said second radial positions having a first section with a curvilinear shape with an outer radius of curvature transitioning into a second section with an inner radius of curvature and said tabs having an upper neck portion and wherein said lower blocker portion prevents removal of the surgical screws from said body unless a driver contacts said tabs' upper neck portions to cause said lower blocker portions to be urged outwardly.

9. A surgical screw cartridge system as described in claim 8 further including an alignment cap for positioning the screwdriver with respect to said surgical screw within said body, said alignment cap being more adjacent to said tabs' upper neck portions than said tabs' lower blocker portions.

10. A surgical screw cartridge system as described in claim 9 wherein said tabs are is connected with said alignment cap.

* * * * *